(12) United States Patent
Goddard et al.

(10) Patent No.: US 9,962,251 B2
(45) Date of Patent: May 8, 2018

(54) DEVICES AND METHODS FOR DELIVERING IMPLANTS

(71) Applicant: Boston Scientific Scimed, Inc., Maple Grove, MN (US)

(72) Inventors: James M. Goddard, Pepperell, MA (US); Jamie Li, Lexington, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 565 days.

(21) Appl. No.: 14/514,052

(22) Filed: Oct. 14, 2014

(65) Prior Publication Data
US 2015/0112127 A1 Apr. 23, 2015

Related U.S. Application Data

(60) Provisional application No. 61/892,057, filed on Oct. 17, 2013.

(51) Int. Cl.
*A61F 2/00* (2006.01)
*A61B 17/06* (2006.01)
(Continued)

(52) U.S. Cl.
CPC ........ *A61F 2/0063* (2013.01); *A61B 17/0401* (2013.01); *A61B 17/0469* (2013.01);
(Continued)

(58) Field of Classification Search
CPC .............. A61F 2/0063; A61F 2/0045; A61F 2002/0072; A61B 2017/06042; A61B 17/0469; A61B 2017/047; A61B 2017/06028; A61B 17/06109; A61B 2017/00805; A61B 2017/00336; A61B 2017/0608; A61B 2017/061;
(Continued)

(56) References Cited

U.S. PATENT DOCUMENTS

| 669,034 A | 2/1901 | Manly |
| 3,123,077 A | 3/1964 | Alcamo |

(Continued)

FOREIGN PATENT DOCUMENTS

| CN | 102802560 A | 11/2012 |
| EP | 0412664 A1 | 2/1991 |

(Continued)

OTHER PUBLICATIONS

First Office Action for Chinese Application 201480056432.2, dated Nov. 28, 2016, 16 pages.
(Continued)

*Primary Examiner* — Navin Natnithithadha
*Assistant Examiner* — Sunita Reddy
(74) *Attorney, Agent, or Firm* — Brake Hughes Bellermann LLP

(57) ABSTRACT

A medical device assembly includes an implant having a support portion, and an arm portion and a dilator. The medical device assembly further includes a first suture having a first portion coupled to the arm portion of the implant, and a second portion coupled to the dilator. In addition, the assembly includes a second suture having a first portion coupled to the arm portion of the implant, and a second portion coupled to the dilator.

15 Claims, 11 Drawing Sheets

(51) Int. Cl.
*A61B 17/04* (2006.01)
*A61B 17/00* (2006.01)

(52) U.S. Cl.
CPC .... *A61B 17/0482* (2013.01); *A61B 17/06109* (2013.01); *A61F 2/0045* (2013.01); *A61B 17/0485* (2013.01); *A61B 2017/00336* (2013.01); *A61B 2017/00805* (2013.01); *A61B 2017/047* (2013.01); *A61B 2017/061* (2013.01); *A61B 2017/0608* (2013.01); *A61B 2017/06028* (2013.01); *A61B 2017/06042* (2013.01); *A61F 2002/0072* (2013.01)

(58) Field of Classification Search
CPC ............ A61B 17/0401; A61B 17/0482; A61B 17/0485; A61B 2002/0072
USPC .............................................. 600/37, 29–32
See application file for complete search history.

(56) References Cited

U.S. PATENT DOCUMENTS

| | | | |
|---|---|---|---|
| 4,324,331 A | 4/1982 | Ignasiak | |
| 4,775,380 A | 10/1988 | Seedhom et al. | |
| 4,792,336 A | 12/1988 | Hlavacek et al. | |
| 4,919,667 A | 4/1990 | Richmond | |
| 4,935,027 A | 6/1990 | Yoon | |
| 4,998,912 A | 3/1991 | Scarbrough et al. | |
| 5,013,292 A | 5/1991 | Lemay | |
| 5,082,112 A | 1/1992 | Dunklee | |
| 5,108,406 A | 4/1992 | Lee | |
| 5,149,329 A | 9/1992 | Richardson | |
| 5,217,466 A | 6/1993 | Hasson | |
| 5,217,486 A | 6/1993 | Rice et al. | |
| 5,217,494 A | 6/1993 | Coggins et al. | |
| 5,263,969 A | 11/1993 | Phillips | |
| 5,356,432 A | 10/1994 | Rutkow et al. | |
| 5,362,294 A | 11/1994 | Seitzinger | |
| 5,383,905 A | 1/1995 | Golds et al. | |
| 5,405,359 A | 4/1995 | Pierce | |
| 5,425,747 A | 6/1995 | Brotz | |
| 5,458,636 A | 10/1995 | Brancato | |
| 5,485,917 A | 1/1996 | Early | |
| 5,534,008 A | 7/1996 | Acksel | |
| 5,562,678 A | 10/1996 | Booker | |
| 5,562,689 A | 10/1996 | Green et al. | |
| 5,584,859 A | 12/1996 | Brotz | |
| 5,643,311 A | 7/1997 | Smith et al. | |
| 5,683,402 A | 11/1997 | Cosgrove et al. | |
| 5,702,397 A | 12/1997 | Goble et al. | |
| 5,741,277 A | 4/1998 | Gordon et al. | |
| 5,840,011 A | 11/1998 | Landgrebe et al. | |
| 5,899,909 A | 5/1999 | Claren et al. | |
| 5,931,855 A | 8/1999 | Buncke | |
| 5,948,001 A | 9/1999 | Larsen | |
| 5,976,127 A | 11/1999 | Lax | |
| 6,010,447 A | 1/2000 | Kardjian et al. | |
| 6,012,580 A | 1/2000 | Peters et al. | |
| 6,039,686 A | 3/2000 | Kovac | |
| 6,042,534 A | 3/2000 | Gellman et al. | |
| 6,042,536 A | 3/2000 | Tihon et al. | |
| 6,042,592 A | 3/2000 | Schmitt | |
| 6,044,847 A | 4/2000 | Carter et al. | |
| 6,197,036 B1 | 3/2001 | Tripp et al. | |
| 6,200,330 B1 | 3/2001 | Benderev et al. | |
| 6,221,005 B1 | 4/2001 | Bruckner et al. | |
| 6,267,772 B1 | 7/2001 | Mulhauser et al. | |
| 6,273,852 B1 | 8/2001 | Lehe et al. | |
| 6,306,079 B1 | 10/2001 | Trabucco | |
| 6,322,492 B1 | 11/2001 | Kovac | |
| 6,328,686 B1 | 12/2001 | Kovac | |
| 6,375,662 B1 | 4/2002 | Schmitt | |
| 6,382,214 B1 | 5/2002 | Raz et al. | |
| 6,406,423 B1 | 6/2002 | Scetbon | |
| 6,478,727 B2 | 11/2002 | Scetbon | |
| 6,491,703 B1 | 12/2002 | Ulmsten | |
| 6,502,578 B2 | 1/2003 | Raz et al. | |
| 6,506,190 B1 | 1/2003 | Walshe | |
| 6,544,273 B1 | 4/2003 | Harari et al. | |
| 6,547,800 B2 | 4/2003 | Foerster et al. | |
| 6,565,580 B1 | 5/2003 | Beretta | |
| 6,575,998 B2 | 6/2003 | Beyar | |
| 6,582,443 B2 | 6/2003 | Cabak et al. | |
| 6,592,515 B2 | 7/2003 | Thierfelder et al. | |
| 6,592,610 B2 | 7/2003 | Beyar | |
| 6,595,911 B2 | 7/2003 | Lovuolo | |
| 6,596,001 B2 | 7/2003 | Stormby et al. | |
| 6,599,235 B2 | 7/2003 | Kovac | |
| 6,599,310 B2 | 7/2003 | Leung et al. | |
| 6,612,977 B2 | 9/2003 | Staskin et al. | |
| 6,638,209 B2 | 10/2003 | Landgrebe | |
| 6,638,210 B2 | 10/2003 | Berger | |
| 6,638,211 B2 | 10/2003 | Suslian et al. | |
| 6,641,524 B2 | 11/2003 | Kovac | |
| 6,641,525 B2 | 11/2003 | Rocheleau et al. | |
| 6,648,899 B2 | 11/2003 | Kalinski et al. | |
| 6,648,921 B2 | 11/2003 | Anderson et al. | |
| 6,652,450 B2 | 11/2003 | Neisz et al. | |
| 6,666,817 B2 | 12/2003 | Li | |
| 6,669,706 B2 | 12/2003 | Schmitt et al. | |
| 6,669,735 B1 | 12/2003 | Pelissier | |
| 6,673,010 B2 | 1/2004 | Skiba et al. | |
| 6,691,711 B2 | 2/2004 | Raz et al. | |
| 6,695,855 B1 | 2/2004 | Gaston | |
| 6,702,827 B1 | 3/2004 | Lund et al. | |
| 6,730,110 B1 | 5/2004 | Harari et al. | |
| 6,746,455 B2 | 6/2004 | Beyar et al. | |
| 6,752,814 B2 | 6/2004 | Gellman et al. | |
| 6,755,781 B2 | 6/2004 | Gellman | |
| 6,808,487 B2 | 10/2004 | Migliari | |
| 6,830,052 B2 | 12/2004 | Carter et al. | |
| 6,848,152 B2 | 2/2005 | Genova et al. | |
| 6,881,184 B2 | 4/2005 | Zappala | |
| 6,890,338 B1 | 5/2005 | Davis et al. | |
| 6,908,425 B2 | 6/2005 | Luscombe | |
| 6,911,003 B2 | 6/2005 | Anderson et al. | |
| 6,911,034 B2 | 6/2005 | Nobles et al. | |
| 6,932,759 B2 | 8/2005 | Kammerer et al. | |
| 6,936,052 B2 | 8/2005 | Gellman et al. | |
| 6,946,003 B1 | 9/2005 | Wolowacz et al. | |
| 6,953,428 B2 | 10/2005 | Gellman et al. | |
| 6,960,160 B2 | 11/2005 | Browning | |
| 6,971,986 B2 | 12/2005 | Staskin et al. | |
| 6,991,597 B2 | 1/2006 | Gellman et al. | |
| 7,011,688 B2 | 3/2006 | Gryska et al. | |
| 7,025,772 B2 | 4/2006 | Gellman et al. | |
| 7,048,682 B2 | 5/2006 | Neisz et al. | |
| 7,056,333 B2 | 6/2006 | Walshe | |
| 7,070,556 B2 | 7/2006 | Anderson et al. | |
| 7,070,558 B2 | 7/2006 | Gellman et al. | |
| 7,083,568 B2 | 8/2006 | Neisz et al. | |
| 7,083,637 B1 | 8/2006 | Tannhauser | |
| 7,090,686 B2 | 8/2006 | Nobles et al. | |
| 7,094,199 B2 | 8/2006 | Petros et al. | |
| 7,112,171 B2 | 9/2006 | Rocheleau et al. | |
| 7,112,210 B2 | 9/2006 | Ulmsten et al. | |
| 7,122,039 B2 | 10/2006 | Chu | |
| 7,131,943 B2 | 11/2006 | Kammerer | |
| 7,131,944 B2 | 11/2006 | Jacquetin | |
| 7,198,597 B2 | 4/2007 | Siegel et al. | |
| 7,204,801 B2 | 4/2007 | Grocela | |
| 7,204,802 B2 | 4/2007 | De Leval | |
| 7,223,229 B2 | 5/2007 | Inman et al. | |
| 7,226,407 B2 | 6/2007 | Kammerer et al. | |
| 7,226,408 B2 | 6/2007 | Harai et al. | |
| 7,229,453 B2 | 6/2007 | Anderson et al. | |
| 7,235,043 B2 | 6/2007 | Gellman et al. | |
| 7,244,260 B2 | 7/2007 | Koseki | |
| 7,244,759 B2 | 7/2007 | Muller et al. | |
| 7,267,645 B2 | 9/2007 | Anderson et al. | |
| 7,291,104 B2 | 11/2007 | Neisz et al. | |
| 7,351,197 B2 | 4/2008 | Montpetit et al. | |
| 7,361,138 B2 | 4/2008 | Wagner et al. | |
| 7,364,541 B2 | 4/2008 | Chu et al. | |

(56) References Cited

U.S. PATENT DOCUMENTS

| | | |
|---|---|---|
| 7,402,133 B2 | 7/2008 | Chu et al. |
| 7,413,540 B2 | 8/2008 | Gellman et al. |
| 8,430,807 B2 | 4/2013 | Chu |
| 2002/0010123 A1 | 1/2002 | Schmiedel et al. |
| 2002/0091373 A1 | 7/2002 | Berger |
| 2002/0128045 A1 | 9/2002 | Chang et al. |
| 2002/0147382 A1 | 10/2002 | Neisz et al. |
| 2002/0151909 A1 | 10/2002 | Gellman et al. |
| 2002/0156489 A1 | 10/2002 | Gellman et al. |
| 2003/0004395 A1 | 1/2003 | Therin |
| 2003/0125023 A1 | 7/2003 | Fishler |
| 2003/0149012 A1 | 8/2003 | Strong et al. |
| 2003/0220123 A1 | 11/2003 | Motohashi |
| 2003/0225123 A1 | 12/2003 | Auerbach et al. |
| 2004/0006123 A1 | 1/2004 | Alkan et al. |
| 2004/0039453 A1* | 2/2004 | Anderson .......... A61B 17/0401 623/23.72 |
| 2004/0073123 A1 | 4/2004 | Hessel et al. |
| 2004/0106847 A1 | 6/2004 | Benderev |
| 2004/0181123 A1 | 9/2004 | Alferness et al. |
| 2004/0225181 A1 | 11/2004 | Chu et al. |
| 2004/0230123 A1 | 11/2004 | White et al. |
| 2004/0249397 A1* | 12/2004 | Delorme ................ A61B 17/06 606/151 |
| 2004/0249473 A1* | 12/2004 | Delorme ................ A61B 17/06 623/23.64 |
| 2005/0004123 A1 | 1/2005 | Gesing et al. |
| 2005/0038123 A1 | 2/2005 | Henegar |
| 2005/0075123 A1 | 4/2005 | Jin et al. |
| 2005/0080123 A1 | 4/2005 | Watanabe et al. |
| 2005/0090123 A1 | 4/2005 | Nishimura et al. |
| 2005/0096123 A1 | 5/2005 | Cregan et al. |
| 2005/0101123 A1 | 5/2005 | Kumada et al. |
| 2005/0107123 A1 | 5/2005 | Ishii et al. |
| 2005/0107660 A1 | 5/2005 | Valtchev |
| 2005/0131123 A1 | 6/2005 | Hawrylko et al. |
| 2005/0177022 A1 | 8/2005 | Chu et al. |
| 2005/0192123 A1 | 9/2005 | Bissonnette et al. |
| 2005/0245787 A1 | 11/2005 | Cox et al. |
| 2005/0250123 A1 | 11/2005 | Yang et al. |
| 2005/0256123 A1 | 11/2005 | Marlow et al. |
| 2005/0261123 A1 | 11/2005 | Alt et al. |
| 2005/0277123 A1 | 12/2005 | Weiss et al. |
| 2006/0015123 A1 | 1/2006 | Fencl et al. |
| 2006/0025123 A1 | 2/2006 | Majmundar et al. |
| 2006/0041123 A1 | 2/2006 | Axten et al. |
| 2006/0058123 A1 | 3/2006 | Publicover |
| 2006/0069123 A1 | 3/2006 | Xia et al. |
| 2006/0089123 A1 | 4/2006 | Frank |
| 2006/0089525 A1 | 4/2006 | Mamo et al. |
| 2006/0122123 A1 | 6/2006 | Chaudhary et al. |
| 2006/0173123 A1 | 8/2006 | Yang et al. |
| 2006/0183966 A1 | 8/2006 | Neisz et al. |
| 2006/0195010 A1 | 8/2006 | Arnal |
| 2006/0205123 A1 | 9/2006 | Holmes et al. |
| 2006/0211123 A1 | 9/2006 | Ker et al. |
| 2006/0229123 A1 | 10/2006 | Owen |
| 2006/0260123 A1 | 11/2006 | McAllister et al. |
| 2006/0264123 A1 | 11/2006 | Sergi |
| 2006/0287571 A1 | 12/2006 | Gozzi et al. |
| 2007/0015953 A1 | 1/2007 | MacLean |
| 2007/0123915 A1 | 5/2007 | Kammerer et al. |
| 2007/0203508 A1 | 8/2007 | White et al. |
| 2007/0276123 A1 | 11/2007 | Larsen et al. |
| 2008/0091221 A1 | 4/2008 | Brubaker et al. |
| 2008/0103351 A1* | 5/2008 | Montpetit .......... A61B 17/0401 600/30 |
| 2008/0140218 A1* | 6/2008 | Staskin .............. A61B 17/0401 623/23.72 |
| 2008/0287732 A1 | 11/2008 | Kuntz |
| 2009/0171124 A1 | 7/2009 | Ishida et al. |
| 2009/0171140 A1 | 7/2009 | Chu |
| 2009/0171142 A1 | 7/2009 | Chu |
| 2009/0216075 A1 | 8/2009 | Bell et al. |
| 2010/0268018 A1 | 10/2010 | Chu et al. |
| 2012/0059217 A1 | 3/2012 | Goldberg et al. |

FOREIGN PATENT DOCUMENTS

| | | |
|---|---|---|
| EP | 1201189 A2 | 5/2002 |
| EP | 1508305 A2 | 2/2005 |
| EP | 1520554 A2 | 4/2005 |
| GB | 670349 | 4/1952 |
| JP | 2006069078 A | 3/2006 |
| JP | 2007097994 A | 4/2007 |
| JP | 2007149348 A | 6/2007 |
| JP | 2008523926 T | 7/2008 |
| JP | 2009527272 A | 7/2009 |
| JP | 2009539558 A | 11/2009 |
| JP | 2011508632 A | 3/2011 |
| WO | 98/35632 A1 | 8/1998 |
| WO | 02/78571 A2 | 10/2002 |
| WO | 03/092546 A2 | 11/2003 |
| WO | 03/096929 A1 | 11/2003 |
| WO | 2003096929 A1 | 11/2003 |
| WO | 2004/091442 A2 | 10/2004 |
| WO | 2005/110274 A2 | 11/2005 |
| WO | 2005/122721 A2 | 12/2005 |
| WO | 2006/046950 A1 | 5/2006 |
| WO | 2006/069078 A2 | 6/2006 |
| WO | 2006/108045 A2 | 10/2006 |
| WO | 2007/016698 A2 | 2/2007 |
| WO | 2007/017274 A2 | 2/2007 |
| WO | 2007/019374 A2 | 2/2007 |
| WO | 2007059199 A2 | 5/2007 |
| WO | 2007059368 A1 | 5/2007 |
| WO | 2007/097994 A2 | 8/2007 |
| WO | 2007/149348 A2 | 12/2007 |
| WO | 2009/086355 A2 | 7/2009 |
| WO | 2009/086369 A2 | 7/2009 |
| WO | 2012129391 A1 | 9/2012 |
| WO | 2015057833 | 4/2015 |

OTHER PUBLICATIONS

International Preliminary Report on Patentability for PCT Application No. PCT/US2014/060683, dated Apr. 28, 2016, 8 pages.
International Search Report and Written Opinion for PCT Application No. PCT/US2014/060683, dated Jan. 8, 2015, 12 Pages.
Second Office Action for Chinese Application No. 201480056432.2, dated Jun. 6, 2017, 8 pages.
Office Action for Japanese Application No. 2016-523936, dated Mar. 21, 2017, 9 pages.
Notice of Allowance for CN Application No. 201480056432.2, dated Sep. 6, 2017, 8 pages.

* cited by examiner

DEVICES AND METHODS FOR DELIVERING IMPLANTS

CROSS-REFERENCE TO RELATED APPLICATION

This application is a Nonprovisional of, and claims priority to, U.S. Patent Application No. 61/892,057, filed on Oct. 17, 2013, entitled "DEVICES AND METHODS FOR DELIVERING IMPLANTS", which is incorporated by reference herein in its entirety.

TECHNICAL FIELD

Some embodiments generally relate to medical devices, and more particularly to implants and methods for delivering implants within a pelvic region of a patient to treat various pelvic dysfunctions.

BACKGROUND

A variety of medical procedures are performed to treat various female pelvic dysfunctions, including procedures to treat urinary incontinence, and correcting various prolapse conditions, such as uterine prolapse, cystoceles, rectoceles, and vaginal vault prolapse.

Women often experience vaginal prolapses due to age or other factors. For example, women may experience a cystocele, a rectocele and/or a hysterocele. A cystocele occurs when the bladder bulges into the vagina, and a rectocele occurs when the rectum bulges into the vagina. A hysterocele occurs when the uterus descends into the vagina. An enterocele (small bowel prolapse) can also occur when the small bowel pushes through the upper wall of the vagina. It is relatively common for a hysterocele and cystocele, or hysterocele and rectocele, or other combinations thereof, to occur at the same time. It is also common for different types of prolapse to occur in relatively quick succession.

Some treatments include suturing procedures or the use of implants for support or suspension. A hysterocele is often treated with a hysterectomy followed by a vaginal vault suspension. Various devices and procedures are used to deliver and secure pelvic implants within a variety of different anatomical structures within a pelvic region. Implants can be delivered to a pelvic region through one or more vaginal incisions, and/or through exterior incisions (such as abdominal incisions) in the patient.

Some implants differ in many ways including size, shape, material, number and location of arm portions, and in the method in which they are delivered and placed within a pelvic region. For example, various implants include couplings or tack welds between certain elements, and the physicians are required to break these coupling or tack welds while placing the implant within the pelvic region. However, in some cases, the breaking of such couplings or tack welds is not always easy and does not always have a reproducible result. In some cases, the breaking of the couplings or tack welds may lead to damage to the surrounding tissue. Thus, it may be desirable to provide enhanced pelvic implants and delivery processes associated with such implants, such that implants can be released smoothly without the use of couplings or tack welds; thereby, reducing or preventing damage to the body of the patient or to the implant during implantation.

SUMMARY

In an embodiment, a medical device assembly includes an implant having a support portion and an arm portion. The medical device assembly further includes a dilator, a first suture and a second suture. The first suture has a first portion coupled to the arm portion of the implant, and a second portion coupled to the dilator. The second suture has a first portion coupled to the arm portion of the implant, and a second portion coupled to the dilator. The medical device assembly further includes a sleeve coupled to the dilator. The sleeve defines a cavity, and at least a portion of the arm portion of the implant is disposed within the cavity defined by the sleeve.

In another embodiment, a medical device assembly comprises an implant having a support portion and an arm portion. The medical device assembly further includes a dilator, a first suture and a second suture. The first suture has a first portion coupled to the arm portion of the implant and a second portion coupled to the dilator. The second suture has a first portion coupled to the arm portion of the implant and a second portion coupled to the dilator. The medical device assembly further includes a sleeve coupled to the dilator. The sleeve defines a cavity, and at least a portion of the arm portion of the implant is disposed within the cavity defined by the sleeve. The second suture is woven through a portion of the sleeve and a portion of the arm portion of the implant.

In a further embodiment, a method of placing an implant within a body of a patient is disclosed. The method includes inserting an assembly into a body of a patient such that a first portion of the assembly is disposed within the body of the patient and a second portion of the assembly is disposed outside of the body of the patient. The assembly includes an implant having a support portion and an arm portion, a dilator, a first suture having a first portion coupled to the arm portion of the implant and a second portion coupled to the dilator, and a second suture having a first portion coupled to the arm portion of the implant and a second portion coupled to the dilator. The first suture forms a loop and at least a portion of the first suture is woven through a portion of the arm portion of the implant. The method further includes cutting the first suture and then cutting the second suture, to separate the dilator from the implant such that at least a portion of the implant remains within the body of the patient.

DETAILED DESCRIPTION

Figure 1:
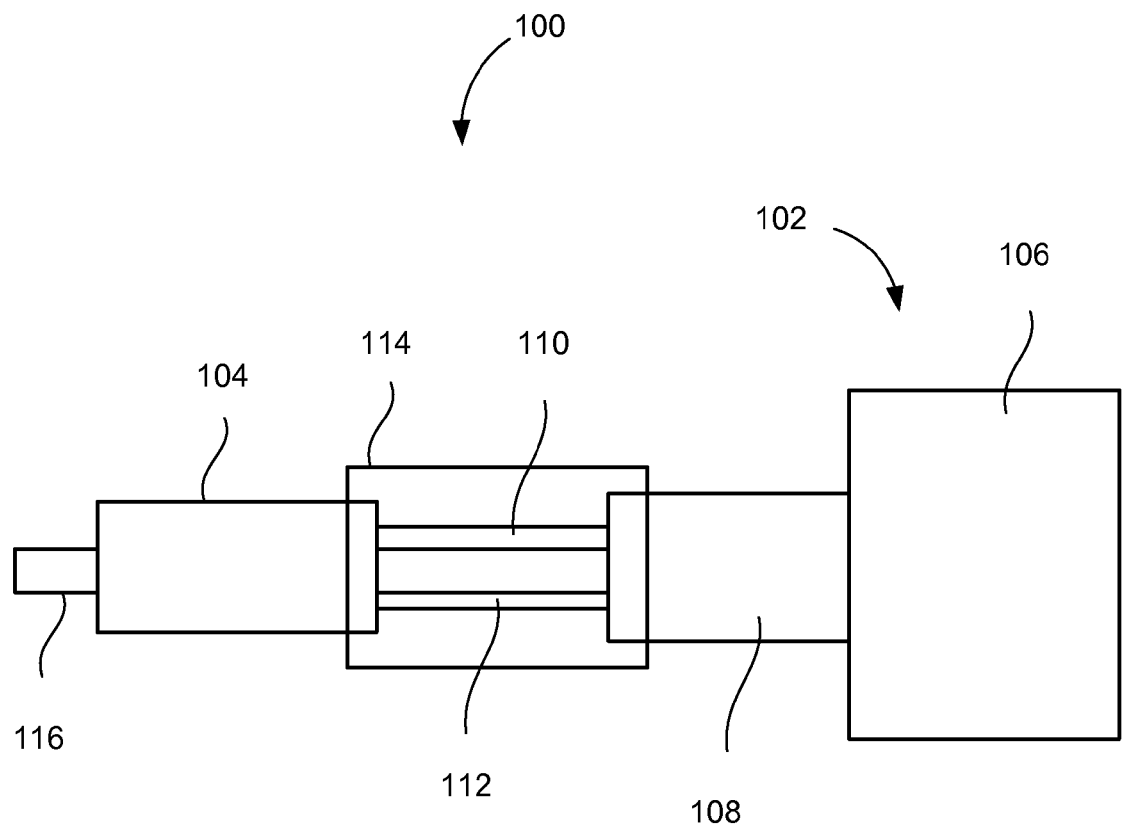
FIG. 1 is a schematic view of a medical device assembly, according to an embodiment of the invention.

In some embodiments, a medical device assembly includes an implant and a dilator. The implant has a support portion and an arm portion extending from the support portion. The support portion is configured to support a portion of a body of a patient. The arm portion is configured to be inserted into a tissue of the patient. The medical device assembly further includes a first suture and a second suture, having a first portion coupled to the arm portion of the implant, and a second portion coupled to the dilator. A sleeve coupled to the dilator defines a cavity, and at least a portion of the arm portion of the implant disposed within the cavity defined by the sleeve. The sleeve facilitates insertion of the implant in the body of a patient. The first suture and the second suture keep the arm portion in position within the sleeve, and enable smoother delivery of the implant in the body of the patient.

In some embodiments, a medical device assembly includes an implant having a support portion and an arm portion, a dilator, a sleeve coupled to the dilator, a first suture having a first portion coupled to the arm portion of the implant and a second portion coupled to the dilator, and a second suture having a first portion coupled to the arm portion of the implant and a second portion coupled to the dilator. The second suture is woven through a portion of the sleeve and a portion of the arm portion of the implant. The sleeve defines a cavity. At least a portion of the arm portion of the implant is disposed within the cavity defined by the sleeve. At least a portion of the first suture is disposed within the cavity defined by the sleeve.

Some embodiments are directed to a method of placing an implant within a body of a patient. The method includes inserting an assembly into a body of a patient, such that a first portion of the assembly is disposed within the body of the patient, and a second portion of the assembly is disposed outside of the body of the patient. The assembly includes an implant having a support portion and an arm portion, a dilator, a first suture having a first portion coupled to the arm portion of the implant and a second portion coupled to the dilator, and a second suture having a first portion coupled to the arm portion of the implant and a second portion coupled to the dilator. Thereafter, the method includes cutting the first suture and cutting the second suture. The dilator is then separated from the implant, such that at least a portion of the implant remains within the body of the patient.

As used herein, the terms proximal portion or proximal end refer to the portion or end, respectively, of a device that is closest to a medical practitioner (e.g., a physician) when performing a medical procedure. The terms distal portion or distal end refer to the portion or end, respectively, of the device that is furthest from the physician during a medical procedure. For example, the end of an implant or sleeve first inserted inside the patient's body would be the distal end of the implant or sleeve, while the end of the implant or sleeve to enter the patient's body last would be the proximal end of the medical device.

An implant, according to an embodiment, can be implanted, for example, through a vaginal incision. A procedure to deploy the implant can include a single vaginal incision, such as an anterior vaginal incision. Implants can be delivered to a pelvic region of a patient using a variety of different delivery devices, only some examples of which are described herein. Various delivery aids are also described, some of which can be included as part of an implant (e.g., provided to a physician assembled) and some of which can be coupled to or associated with an implant just prior to implantation. Such delivery aids are typically removed after placing one or more arm portions of an implant at a desired tissue securement location, leaving the arm portion to engage the tissue and support the support portion of the implant. For example, a sleeve assembly can be used to lead an implant or an arm portion of an implant through a tissue in an intracorporeal location (i.e., within the patient's body), such as the sacrospinous ligament or arcus tendineus fasciae pelvis. In other embodiments, a sleeve assembly can be used to lead an implant or an arm portion of an implant through a tissue and to an extracorporeal location (outside the patient's body), such as through an obturator membrane or muscle and out through an exterior incision in the patient.

FIG. 1 is a schematic view of a medical device assembly 100 according to an embodiment. The medical device assembly 100 includes an implant 102 and a dilator 104. The implant 102 includes a support portion 106 and an arm portion 108. The medical device assembly 100 further includes a first suture 110 having a first portion coupled to the arm portion 108, and a second portion coupled to the dilator 104. The medical device assembly 100 also includes a second suture 112 having a first portion coupled to the arm portion 108, and a second portion coupled to the dilator 104. In an embodiment, the first portion of the first suture is coupled to the arm portion of the implant at a first location, the first portion of the second suture is coupled to the arm portion of the implant at a second location different from the first location.

A sleeve 114 is coupled to the dilator 104, and at least a portion of the arm portion 108 is disposed within the cavity defined by the sleeve 114. At least a portion of the first suture 110 and the second suture 112 is disposed within the cavity of the sleeve 114. The medical device assembly 100 further includes an association member 116 coupled to the dilator 104. The association member 116 is configured to associate the medical device assembly 100 to a device, such as a delivery device. The delivery device may be any type of needle of other device that is configured to help facilitate the implantation of the implant 102 within a body of a patient. An example of a delivery device is explained in further detail in conjunction with FIG. 4 below.

The support portion 106 is configured to be placed within a body of a patient, and is configured to support a portion of the human body. The support portion 106 can be a variety of different shapes, sizes and configurations depending on the intended use for the particular implant. In some embodiments, the support portion 106 can have substantially rectangular, square, oval, or elliptical. The support portion 106 can be shaped and sized to support a bladder (e.g., to treat a cystocele) and/or a bladder neck and/or a uterus (e.g., to treat a hysterocele) and/or a rectum (e.g., to treat a rectocele). For example, the support portion 106 may include one or more markings that define portions of the implant 102 (such as portions of the support portion 106) that can be removed by, for example, cutting along one or more markings to resize the implant 102 for implantation.

Further, the support portion 106 can be formed with a mesh material to allow tissue in growth to the implant 102 after implantation. For example, in some cases, the healing tissue may grow through porous openings in an implanted mesh, thereby assimilating the tissue with the mesh and adding structural integrity to the tissue. The mesh may be made of a polymeric material that may include a natural and/or a synthetic material. Exemplary polymeric materials are polypropylene, polyester, polyethylene, nylon, PVC, polystyrene, and the like. The mesh is preferably made of a non-woven polymeric material. In some embodiments, some or all of the support portion 106 can be formed with the Advantage® Mesh or the Polyform™ Synthetic Mesh material, each provided by Boston Scientific Corporation. The Polyform® Synthetic Mesh is a macroporous mesh knitted with uncoated, monofilament polypropylene fiber. The mesh may also be made from a biological material or a cadaveric tissue. Typically, the mesh has smooth surfaces to avoid/reduce irritation on adjacent body tissues during medical interactions. Additionally, the mesh may be stretchable or flexible to adapt to movements of the human body.

The arm portion 108 is coupled to, and extends from, the support portion 106. The arm portion 108 is configured to support the support portion 106 of the implant 102 when the arm portion 108 is inserted into a tissue of the patient. Further, the support portion 106 and the arm portion 108 may be formed from various materials, and may have a variety of different configurations and/or different sizes (e.g., lengths, widths). The arm portion 108 may be formed monolithically with the support portion 106. For example, in some embodiments, the arm portion 108 and the support portion 106 are both formed from a single piece of mesh material.

In other embodiments, the arm portion 108r may be formed separately from the support portion 106 and then coupled to the support portion 106. For example, the arm portion 108 and the support portion 106 can be coupled in an abutting relationship, an overlapping relationship, or can be bridged. The arm portion 108 can be coupled to the support portion 106 by, for example, heat bonding, gluing, using fasteners, and/or sewing. In some embodiments, the arm portion 108 includes a heat seal along its length or a portion of its length to help prevent or reduce stretching of the arm portion 108.

In some embodiments, the arm portion 108 includes tangs configured to help anchor the arm portion within the bodily tissue of the patient. The terms "tanged" or "tangs" as used herein mean roughened or jagged edges or areas, such as can result from cutting a woven or knit mesh material. In other embodiments, the arm portion 108 includes barbs, dimples and/or other protrusions configured to engage the bodily tissue of the patient to help retain the implant 102 in place within the body of the patient. In other embodiments, other mechanisms may be used to couple the arm portion 108 to the bodily tissue.

The sleeve 114 of the implant 102 can be used during the insertion of the implant 102 into a pelvic region to prevent the arm portion 108 from prematurely engaging tissue during the delivery procedure. In some embodiments, the sleeve 114 extends away from the support portion 106 beyond the arm portion 108. The sleeve 114 can also protect the arm portion 108 from damage during delivery. The sleeve 114 can be transparent, semi-transparent, colored, non-colored, or a combination thereof. The sleeve 114 can be, for example, tapered, flat, and/or tubular. The sleeve 114 can be formed for example, with a clear, thin, flexible biocompatible polymer, and be configured to allow a user to examine or view the implant 102 (e.g., the arm portion 108) disposed within the sleeve 114.

The sleeve 114 may be releasably coupled to the arm portion 108, such that the sleeve 114 may be uncoupled from the arm portion 108. For example, in some embodiments, as described in more detail below, sleeve 114 may be coupled to the arm portion 108 via a suture.

The dilator 104 can also be coupled to the sleeve 114, and used to assist in the delivery of the implant 102 to the pelvic region. For example, the dilator 104 can be a variety of different lengths, shapes, diameters, etc. In some embodiments, for example, the dilator 104 has a long, gradual taper. In some cases, a long gradual taper minimizes stress as the dilator 104 is pulled through bodily tissue. The dilator 104 can expand a passage through a tissue during insertion to ease the transition of the opening of the tissue to a cross-section of the sleeve 114 and implant 102. The dilator 104 can be formed of any biocompatible material and can be of any cross-sectional shape.

While the illustrated embodiment shows two sutures 110 and 112, in some embodiments the medical device assembly includes more than two sutures that are configured to couple portions of the assembly together. For example, in some embodiments, the device includes three, four, or more sutures.

In some embodiments, the loops formed by the sutures may be disposed in the same plane. In other embodiments, the sutures may form loops that are not in the same plane. In other words, the sutures may not be entirely disposed in a single plane.

In some embodiments, the medical device assembly includes a single suture that is woven through the implant at a plurality of locations. For example, in some embodiments, a single suture may be woven through the implant at two or more locations. In such embodiments, a single cut in the suture will allow the suture to decouple from the various locations of the implant.

Figure 2:
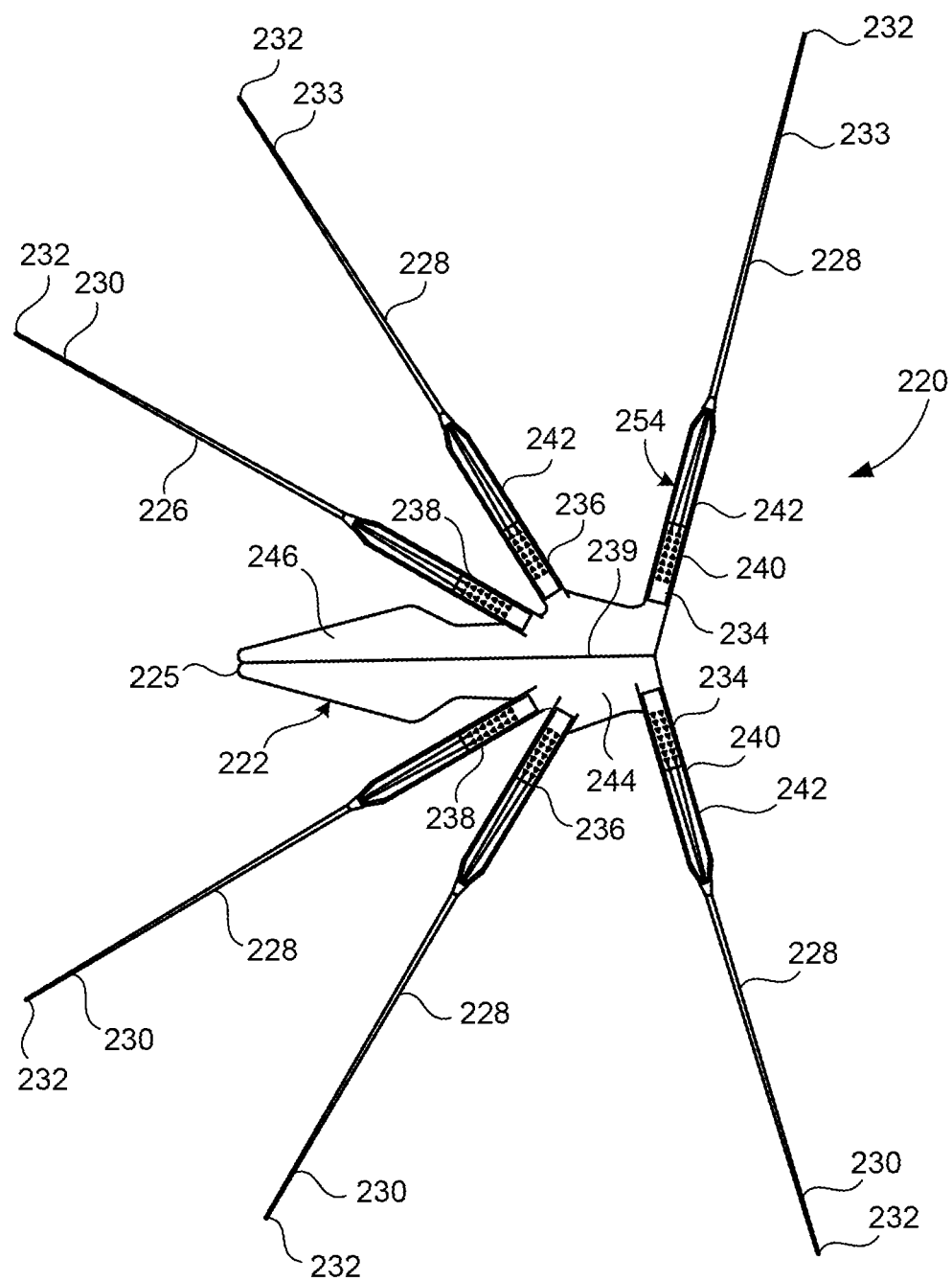
FIG. 2 is a top view of a medical device assembly, according to an embodiment of the invention.

FIG. 2 is a top view of a medical device assembly 200, according to an embodiment of the invention. The medical device assembly 200 includes an implant 220 that further includes six arm portions, including two anterior arm portions 234, two mid arm portions 236, and two posterior arm portions 238. FIG. 2 shows the implant 220 for delivery into a pelvic region through a vaginal incision (e.g., a transvaginal approach) in a retro-pubic direction (behind the pubic bone), or in a pre-pubic direction (in front of the pubic bone). In other embodiments, the implant 220 can be placed in the direction of other anatomical structures as desired. A procedure to deploy a pelvic implant can include a single vaginal incision, such as an anterior vaginal incision and/or a posterior vaginal incision. In some embodiments, a procedure may include making an exterior incision, such as an abdominal incision.

The implant 220 also includes a support portion 222 having an anterior support portion 244, between the anterior arm portions 234 and the mid arm portions 236, and a posterior support portion 246 extending between an end 225 of the implant 220 and the posterior arm portions 238. A center marking 239 is included along a centerline of the support portion 222 that can be used to help position the implant 220 in a desired location within a pelvic region of a patient.

In this embodiment, a length of each of the arm portions 234, 236, 238 is sufficient to secure each arm portion to its intended tissue securement site, but not long enough that the arm portions extend out of the vagina during delivery of the implant 220 into the pelvic region using, for example, a transvaginal approach. For example, the anterior straps 234 of the implant 220 can be placed through, an arcus tendineus, endopelvic fascia, or through tissue or ligaments near or in the pubococcygeus muscle, puborectalis muscle, distal tendineus arch of levator ani muscle or obturator internus or externus muscle, or obturator membrane or other tissue locations within a pelvic region. The mid-straps 236 can each be placed, for example, within a ischio-coccygeus muscle, an arcus tendineus or obturator muscle or membrane. The posterior straps 238 can be placed, for example, in a sacrospinous ligament or coccygeus muscle. In some embodiments, such a length of the arm portions eliminates or reduces the need for trimming large portions of the arm portions after placement, and can also reduce clutter in the vagina and/or pelvic region during placement of the implant 220.

The anterior arm portions 234 can also include textured surfaces such as dimples 240, which may be placed in variety of different configurations. In an embodiment, the anterior arm portions 234 include the dimples 240 on a top and bottom surface of the anterior arm portions 234. The dimples 240 may be disposed in alternating, opposed directions on the top and bottom surfaces of the anterior arm portion 234. The dimples 240 provide added gripping strength to engage surrounding tissue. The number of dimples 240 can vary and can also be included on other straps of the implant 220 and/or some or all of the support portion 222. The straps 234, 236, 238 can also include tangs as described above and/or can include barbs or other protrusions configured to engage bodily tissue.

The dimples 240 can be tapered from their base to an end of the dimple 240. For example, the dimples 240 can be dome-shaped having a larger diameter at their base than a diameter at their tip or end. The dimples 240 can have a width (e.g., a diameter), for example, between about 0.02 cm (0.008 inches) and 0.04 cm (0.02 inches) at their tip and/or at their base. For example, a width of a dimple 240 can be about 0.36 cm (0.14 inches) at its base and narrow or taper to about 0.22 cm (0.087 inches) at an end or tip. A dimple 240 can have a length or height, for example, between about 0.15 cm (0.059 inches) and 0.23 cm (0.091 inches) and can be spaced apart from each other (e.g., from a centerline of one dimple to a center line of another dimple) about 0.6 cm (0.2 inches). In some embodiments, the dimples 240 can also be positioned such that they contact one another, overlap or are spaced at different distances from each other. In other embodiments, the dimples 240 may not be tapered. The arm portions can include, for example, between 1 and 1000 dimples. The dimples 240 can be formed through heat stamping of the arm portion material. In other embodiments, the dimples 240 or other surface textures can be created through other methods such as, for example, stamping, extruding, molding, or weaving.

The sleeves 226 are disposed over or cover at least a portion of each of the arm portions 234, 236, and 238. In some embodiments, the sleeves 226 define a lumen or cavity that receives at least a portion of the arm portions. The dilators 228 can be coupled to the sleeves 226 by, for example, crimping, heat sealing, stitching, stretching, tip tipping, etc. Alternatively, the sleeve 226 can be formed to include a portion that forms a tapered dilator. The dilator 228 can be used to expand or enlarge a passage during insertion through a tissue, to ease the transition to a cross-section or size of the sleeve 226. In the illustrated embodiment, the sleeve 226 is also tapered, which also helps provide a lead-in through the tissue.

Figure 3A:
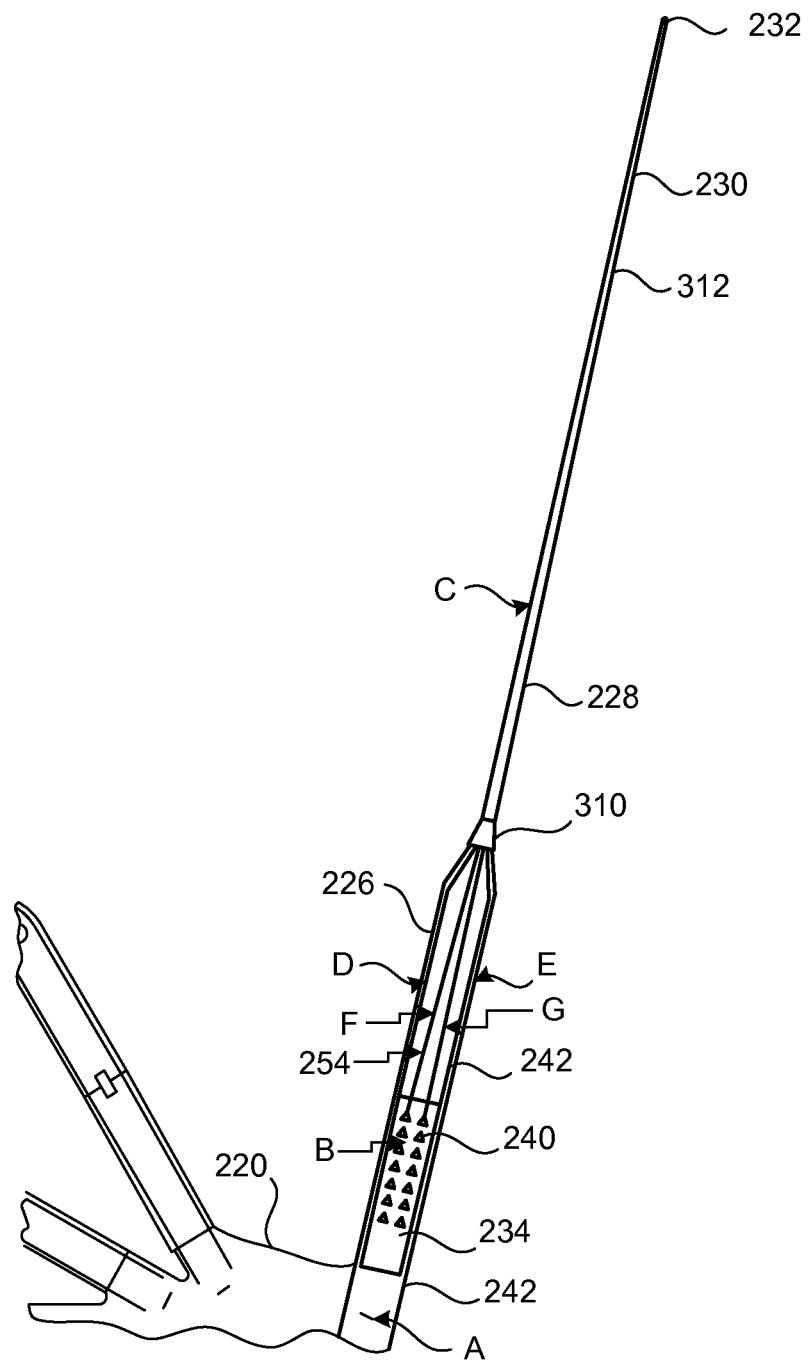
FIG. 3A is a top view of a portion of the medical device assembly of FIG. 2.

The sleeve 226 is secured to the arm portion 234 with a first suture 242 and a second suture 254, as shown in FIG. 3A. Similar, arrangement of the first suture 242 and the second suture 254 may be used to secure the sleeves 226 to the arm portions 236 and 238. FIG. 3A is a top view of a portion of the medical device assembly of FIG. 2. Each of the first suture 242 and the second suture 254 is looped through each of the arm portions 234, 236 and 238. In this embodiment, both the first suture 242 and the second suture 254 are weaved or threaded through the arm portions 234, 236 and 238. For example, as shown for arm portion 234 in FIG. 3A, the first suture 242 is weaved through the arm portion 234 and the implant 220 at location A to form a loop, and the second suture 254 is weaved through the arm portion 234 at location B to form a loop. In the illustrated embodiment, location A is disposed proximal to location B. Accordingly, location B is disposed between the terminal end 234A of the arm portion 234 and location A.

In some embodiments, the first suture 242 is configured to be woven through the arm portion 234 at location A, which may be disposed adjacent to the support portion of the implant. In some embodiments, the first suture 234 helps prevent stretching of the arm portion 234 when the device is placed within the body of patient (as the force of the pulling or placing of the arm portion 234 within the body is located at location A, which may be disposed adjacent to or at the support portion of the implant).

In some embodiments, the second suture 254 is configured to be woven through the arm portion 234 at location B. In some embodiments, the second suture 254 helps prevent the arm portion 234 from getting bunched up or folded within the sleeve 226. Accordingly, in some embodiments, the second suture 254 is configured and arranged to help keep the arm portion 234 flat or planar within the sleeve 226. The second suture 254 may be threaded through or woven through the arm portion 234 any number of times. For example, the second suture 254 may weave in and out of the arm portion 234 two times, three times, or more than three times. Additionally, in some embodiments, the weaving of the first suture 242 and the weaving of the second suture 254 may form a cross or an "x" shape.

As described above, the coupling of the first suture 242 and the second suture 254 can help reduce or prevent arm portions from stretching and can also help prevent the arm portions from being bunched up or folded within the sleeves. The first sutures 242 and the second sutures 254 can alternatively be coupled to the arm portions 234, 236 and 238 by, for example, crimping, heat sealing, stitching, stretching, tip tipping, etc.

Further, in some embodiments, the first suture 242 and the second suture 254 can be threaded to or secured to an arm portion, for example by knotting. The strands of the first suture 242 and the second suture 254 (forming loops through the sleeves 226) extend through an interior lumen (not shown) of the dilators 228, and are crimped closed and heat bonded to an interior wall of the dilators 228 at, for example, a location C.

In some embodiments, the second suture 254 helps to keep the end of the arm portions 234, 236 and 238 in position within the sleeves 226. This ensures that the arm portions 234, 236 and 238 travel with the sleeves 226 as the dilator 104 and the sleeve 226 pass through various tissue sites within the pelvic region during delivery or implantation of the implant 220 within the body of the patient. For example, the anterior straps 234 of the implant 220 can be placed through, an arcus tendineus, endopelvic fascia, or through tissue or ligaments near or in the pubococcygeus muscle, puborectalis muscle, distal tendineus arch of levator ani muscle or obturator internus or externus muscle, or obturator membrane or other tissue locations within a pelvic region. The mid-straps 236 can each be placed, for example, within a ischio-coccygeus muscle, an arcus tendineus or obturator muscle or membrane. The posterior straps 238 can be placed, for example, in a sacrospinous ligament (SSL) or coccygeus muscle.

Once the implant 220 is placed, the physician cuts through a portion of the sleeve 226, one strand of the first suture 242 at, for example, locations D or E, and one strand of the second suture 254 at, for example, locations F or G, thereby allowing removal of the sleeves 226 and the dilator 228 from the body. The sleeve 226 (and dilator 228 that is coupled to the sleeve 226) can then be pulled off of the arm portion 234 by pulling on the sleeve 226 and the uncut strand of each of the first suture 242 and the second suture 254. The cut portions of the first suture 242 and the second suture 254 will also be free to pull through the arm portion 234. Thus, the first suture 242 and the second suture 254 remain secured to the sleeve 226 and will simply unravel or unthread themselves from the arm portion 234. With the sleeve 226 removed from the arm portion 234, the arm portion 234 can engage the surrounding bodily tissue. For example, in some embodiments, the dimples 240 on the arm portion 234 can engage the surrounding tissue into which the arm portion 234 is placed to couple the arm portion 234 to the bodily tissue (the sacrospinous ligament).

Figure 3B:
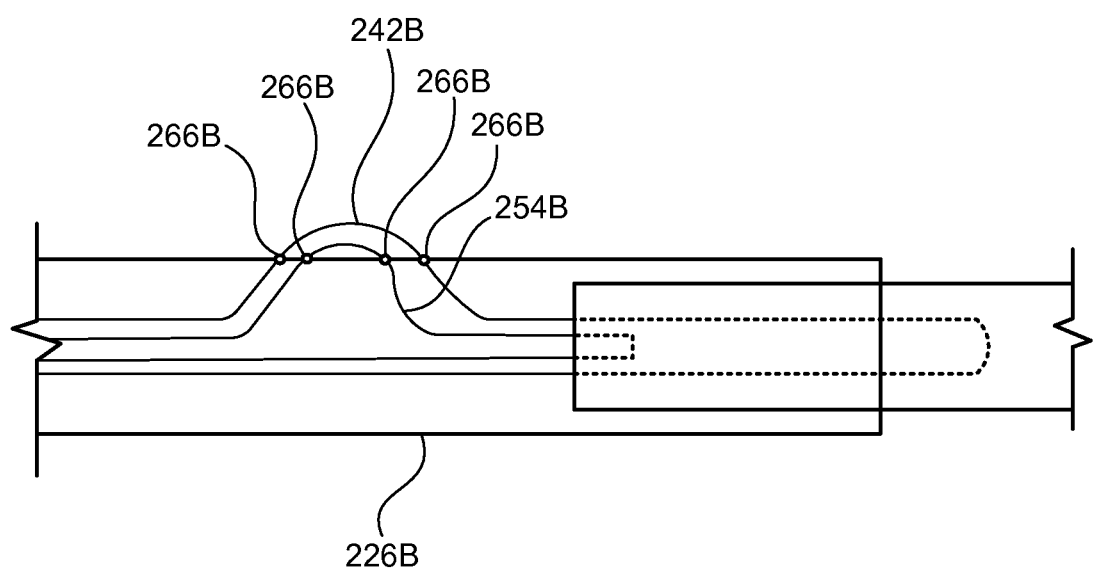
FIG. 3B is a top view of a portion of a medical device assembly according to another embodiment of the invention.

In some embodiments, one strand of the first suture 242 and one strand of the second suture 254 may be cut without cutting the sleeve 226. For example, in some embodiments, the sleeve may define a window or an opening through which the physician may access and cut the strands of the sutures 242 and 254. In other embodiments, as illustrated in FIG. 3B portions of the sutures 242B and 254B may extend through openings 266B defined by the sleeve 226B to allow the physician to access and cut the strands of the sutures 242B and 254B at a location outside of the sleeve 226B (such as outside of the lumen or cavity defined by the sleeve). Accordingly, in some embodiments, the sutures may be cut by the physician at the same time or simultaneously. In some embodiments a suture may be marked to identify a preferred portion or preferred location of the suture to be cut. Such a cutting location may be optimal for removing the suture and/or releasing a sleeve from an arm. In some embodiments a sleeve may be marked at an area that is a preferred location to cut a suture for similar reasons.

In some embodiments, rather than cutting the sutures 242 and 254, the sutures 242 and 254 may be torn or broken. For example, in some embodiments, the sutures 242 and 254 may be pulled to tear or break the sutures 242 and 254. In some embodiments, the sutures 242 and 254 may include a weakened portion that is configured to tear or break when a large pulling force is placed on the sutures. For example, the sutures 242 and 254 may include a portion or section that is thinner than the remainder of the suture or may include portions that have been annealed or have a weak bond between two sections of the suture.

A leader suture 230 is coupled to and extends distally from each of the dilators 228. Alternatively, a leader portion of the first suture 242 and/or the second suture 254 can extend distally from the dilators 228. A trocar needle 232 is coupled to a distal end of each of the leader sutures 230. The trocar needles 232 can be used to associate the implant 220 to a delivery device, such as a BSC Capio® device described below in conjunction with FIG. 4.

The dilators 228 taper from a first diameter at a trailing end 310 to a second, smaller diameter at a leading end 312. The first diameter can be, for example, between about 0.2 and 0.5 cm (0.08 to 0.2 inches), and the second diameter can be, for example, between about 0.03 to 0.2 cm (0.01 to 0.08 inches). For example, in some embodiments, the first diameter can be about 0.37 cm (0.15 inches), and the corresponding second diameter can be, 0.03 cm (0.01 inches). The dilators 228 can be formed, for example, by molding, extruding, casting, sintering, forging, machining, or other known, related art or later developed methods of manufacturing such medical devices.

Figure 4:
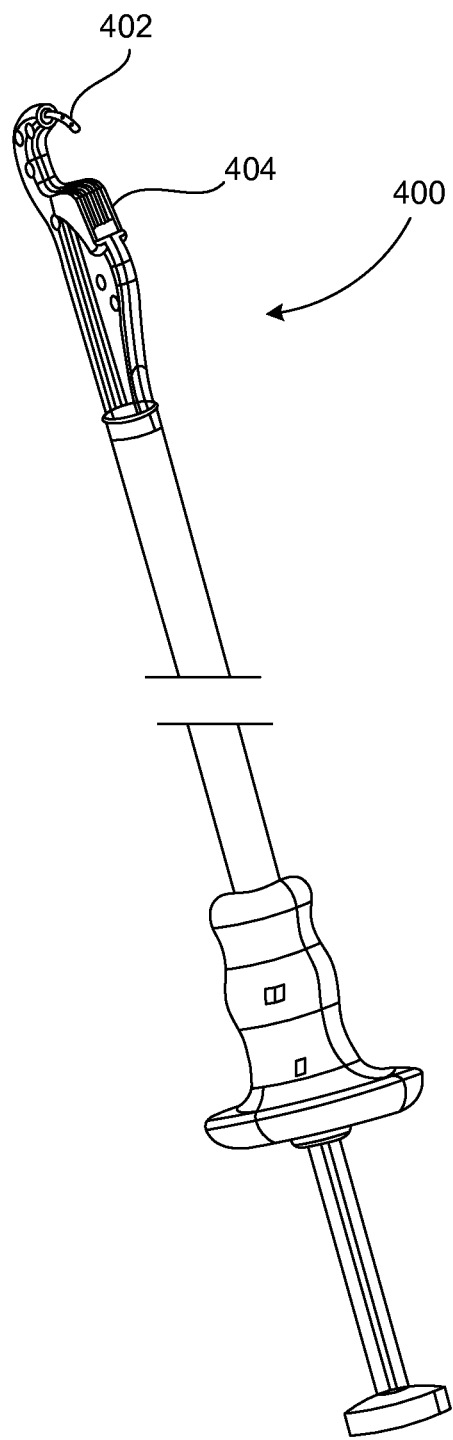
FIG. 4 is a perspective view of a delivery tool for placing a medical device assembly within a body of a patient.

The various arm portions (e.g., 234, 236, 238) of the implant 220 (the medical device assembly 200) can each be delivered through pelvic tissue using, for example, the suturing delivery device 400, as shown in FIG. 4. The trocar needle 232 on one of the arm portions (234, 236, 238) is loaded into the carrier 402 of the delivery device 400. The delivery device 400 can then be used to pass the trocar needle 232 and the arm portion (with the sleeve assembly attached thereto) through a pelvic tissue. Specifically, the carrier 402 of the delivery device 400 is positioned adjacent a selected tissue site, and the carrier 402 is actuated such that the trocar needle 232 pierces through the tissue. The trocar needle 232 and a distal end of the leader suture 230 are caught or retrieved by a catch 404 of the delivery device 400 after passing through the tissue. The delivery device 400 is then removed through the vagina, and the trocar needle 232 is removed from the catch 404. The sleeve 226 and the dilator 228 are pulled through the tissue. For example, a physician can pull the leader suture 230 or the dilator 228 through the tissue, such that the arm portion is disposed within the tissue. This procedure is then repeated for other arm portions of the implant 220. Each arm portion of the implant is pulled through a selected tissue site, and the arm portions are adjusted or moved with respect to the bodily tissue to position and tension the support portion 222. Each arm portion can be delivered sequentially using the same delivery device, or separate delivery devices can be used for some or all of the arm portions. The arm portions 234, 236 and 238 (with the sleeves 226 and the dilators 228 still attached) can be tensioned using visual guidance as the physician observes the positioning of the support portion 222 for the correct tension through the vaginal incision.

A length of the leader suture 230 (measured from a distal end of the tapered portion of the sleeve 226) can vary (see FIG. 3A). For example, in some embodiments, the length of the leader suture 230 is sufficiently long to be placed through a selected tissue anchoring site (after entering the pelvic region via a vaginal incision), and passed out through the vaginal incision, without requiring the tapered portion of the sleeve 226 to engage the selected tissue anchoring site (e.g., after passing through a tissue within the pelvic region). For example, the leader suture 230 can be longer than the length between the SSL and the vaginal opening (VO).

Figure 5:
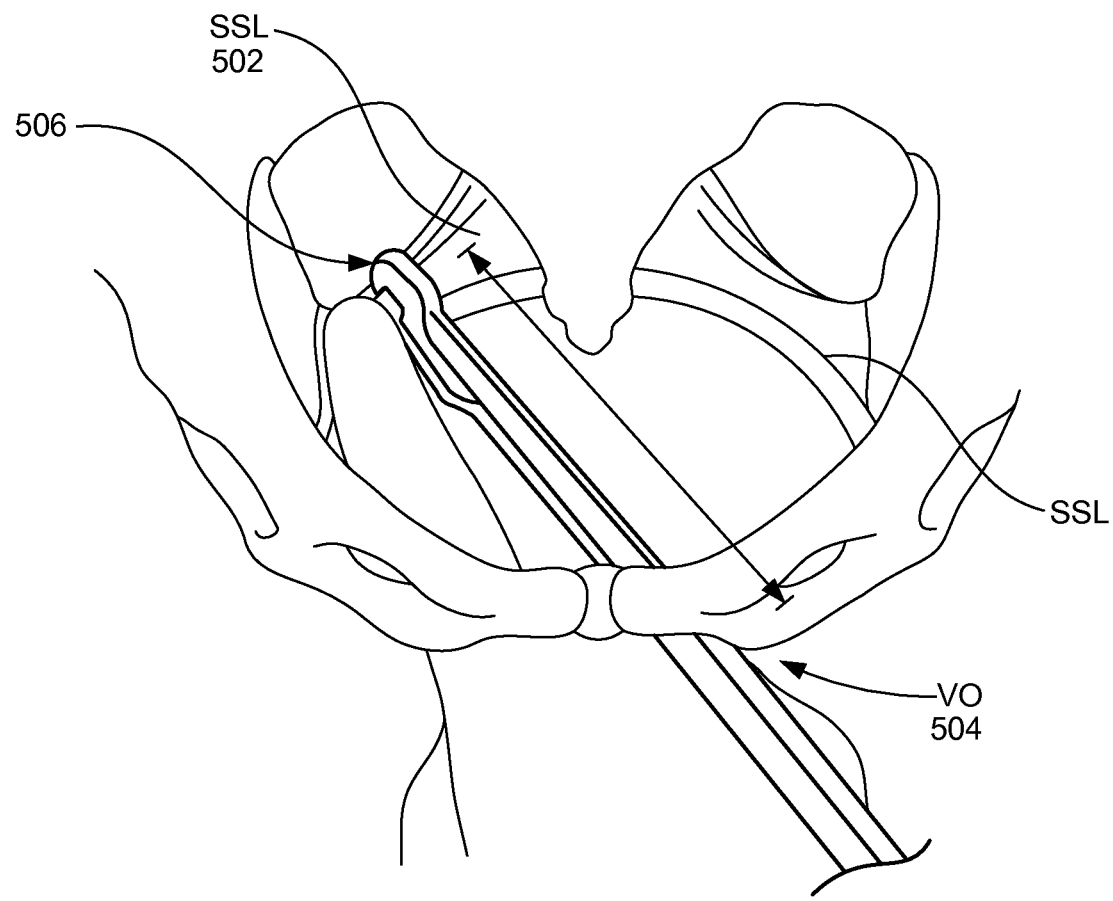
FIG. 5 is a schematic view of a delivery tool placing a medical device assembly within a body of a patient.

FIG. 5 is a schematic illustration of a delivery tool placing a medical device assembly 506 within a body of a patient. As shown in FIG. 5, in some embodiments, the length between the SSL 502 and the VO 504 is approximately 10 cm in length. In other embodiments, the length of the leader suture 230 is sufficiently long to be placed through a selected tissue anchoring site (after entering the pelvic region via a vaginal incision), and passed out through the vaginal incision, without requiring the tapered portion of the sleeve to enter the vagina (e.g., after passing through a tissue within the pelvic region). For example, the leader suture 230 can be longer than twice the length between the SSL 502 and the VO 504. In some embodiments, this is about 20 cm in length. The leader suture 230 having such a length allows the leader suture 230 to be threaded through the selected tissue anchoring site, and passed out through the vaginal incision before the sleeve enters the vaginal incision. Thus, in an embodiment having multiple arm portions and leaders, the leaders can be placed in their respective anchoring sites, and passed out through the vaginal incision before the implant enters the body. This may increase the visibility of the physician to insert the leaders into the multiple anchoring sites within the body.

Figure 6:
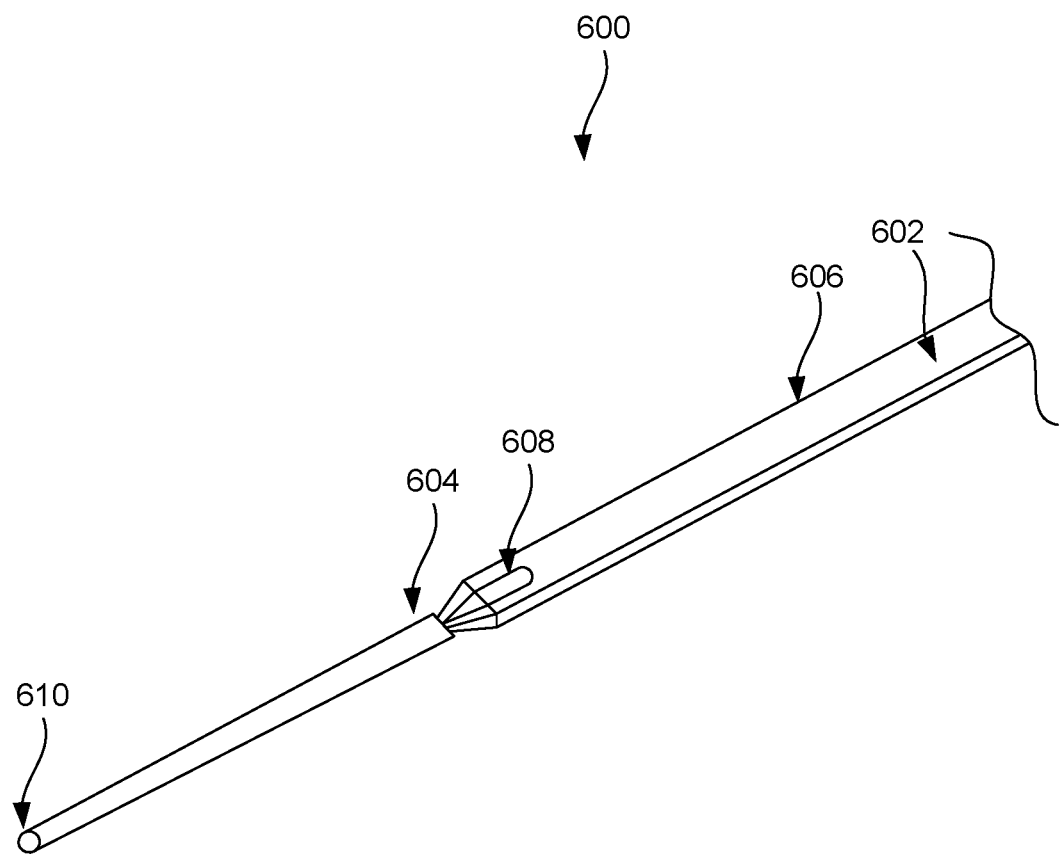
FIG. 6 is a perspective view of a portion of a medical device assembly, according to an embodiment of the invention.

FIG. 6 is a perspective view of a portion of a medical device assembly 600, according to an embodiment of the invention. The medical device assembly 600 includes an arm portion 602, and a sleeve assembly 604 (including a sleeve and a dilator). The arm portion 602 is attached to the sleeve assembly 604 using a first suture 606 and a second suture 608. The sleeve assembly 604 includes a loop connector 610 to associate to a delivery device having an engagement notch, for example, an Obtryx® Curve device, an Obtryx® Halo device, a Curve, or a Lynx® device all manufactured by Boston Scientific Corporation. In other embodiments, the loop connector 610 may be configured to be coupled to a needle passing delivery device. In some embodiments, the medical device assembly 600 is structurally and functionally similar to the medical device assembly 200 described above. In some embodiments, the medical device assembly 600 may be used to help support any portion of the body of the patient. For example, in some embodiments, the assembly 600 may be used to repair a pelvic organ prolapse.

Figure 7:
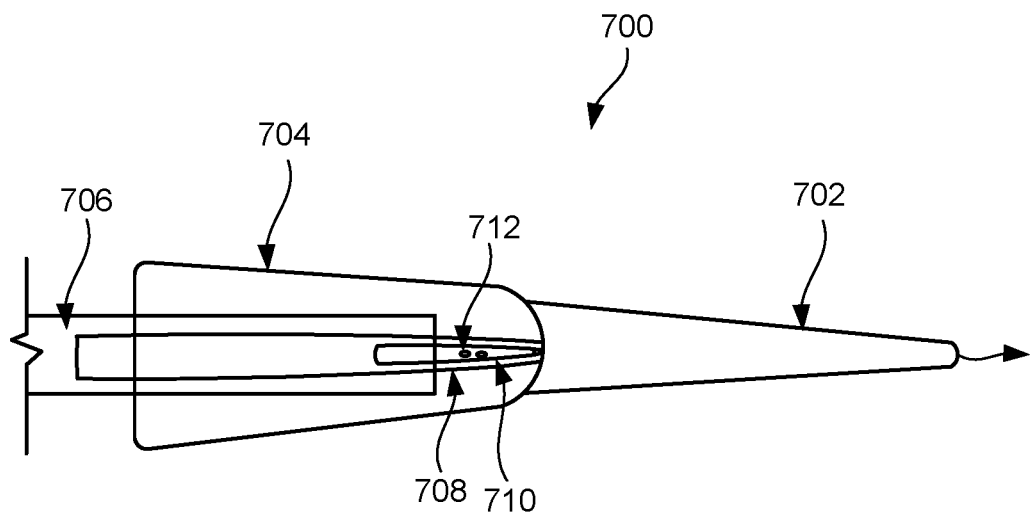
FIG. 7 is a top view of a portion of a medical device assembly, according to an embodiment of the invention.

FIG. 7 is a top view of a portion of a medical device assembly 700, according to an embodiment of the invention. The medical device assembly 700 includes an implant (not illustrated) that may be similar to implant 220, a dilator 702, a sleeve 704 and an arm portion 706 extending from the implant (or a body portion of the implant). A first suture 708 and a second suture 710 releasably connect the arm portion 706 to the dilator 702 and the sleeve 704. The first suture 708 is threaded through the arm portion and forms a loop. The second suture 710 is also threaded through the arm portion and forms a loop.

One or more separators 712 are disposed near a distal end of the sleeve 704, between the two strands of each of the first suture 708 and the second suture 710. The one or more separators 712 maintain separation of the strands of the loops formed by each of the first suture 708 and the second suture 710. The separation of the strands of the first suture 708 and the second suture 710 enables or helps facilitate a cut to be made through only a single strand of each of the first suture 708 and the second suture 710 during the implantation or placement of the implant within the body of the patient. In this embodiment, the one or more separators 712 is a circular seal configuration, which can be formed, for example, by heat stamping two sides of the sleeve 704 together. Other types of separators can alternatively be used, such as for example, a separate component coupled within the sleeve 704, or a heat weld, a head tack, stitch of material or suture, or an adhesive to couple the two sides of the sleeve 704 together at a location between the strands.

Figure 8:
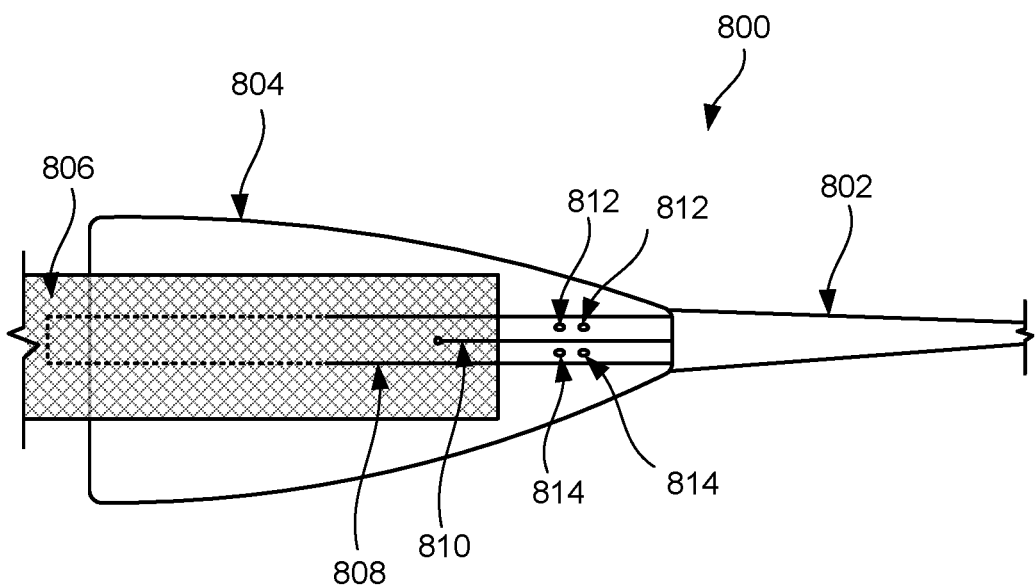
FIG. 8 is a top view of a portion of a medical device assembly, according to an embodiment of the invention.

FIG. 8 is a top view of a portion of a medical device assembly 800, according to an embodiment of the invention. The medical device assembly 800 includes an implant (not illustrated) which may be similar to implant 220, a dilator 802, a sleeve 804 and an arm portion 806. A first suture 808 and a second suture 810 releasably connect the arm portion 806 to the dilator 802 and the sleeve 804. The first suture 808 forms a loop through the arm portion 806 having two strands. The second suture 810 includes a single strand connected to distal end of the arm portion 806. The second suture 810 may be connected to the arm portion 806 using various known, related art or later developed techniques, for example, the second suture 810 may be woven, knotted, heat sealed, coupled with an adhesive to the arm portion 806.

One or more separators 812 and 814 are disposed near a distal end of the sleeve 804. The one or more separators 812 are disposed between a first strand of the first suture 808 and the second suture 810. Similarly, the one or more separators 814 are disposed between a second strand of the first suture 808 a second strand of the first suture 808. As explained in conjunction with FIG. 7 above, the separation of the strands of the first suture 808 enables or helps facilitate a cut to be made through only a single strand of the first suture 808. The sleeve 804 (and the dilator 802 that is coupled to the sleeve 804) can then be pulled off of the arm portion 806 by pulling on the sleeve 804 and the uncut strand of the first suture 808. The cut portion of the first suture 808 will be free to pull through the arm portion 806. Thus, the first suture 808 remains secured to the sleeve 804 and will simply unravel or unthread from the arm portion 806. Additionally, the second suture 810 maybe pulled to break its coupling with the arm portion 806. For example, in some embodiments, the second suture 810 is frictionally coupled to the arm portion 806 via a weave. In some embodiments, the physician may have to exert a predetermined force to break away or release the second suture 810 from the arm portion 806, if the second suture 810 is coupled to the arm portion 806 using a releasable joint such as a heat weld, an adhesive, an interference fit, a controllably tearable portion, and/or mechanical engagements.

Figure 9:
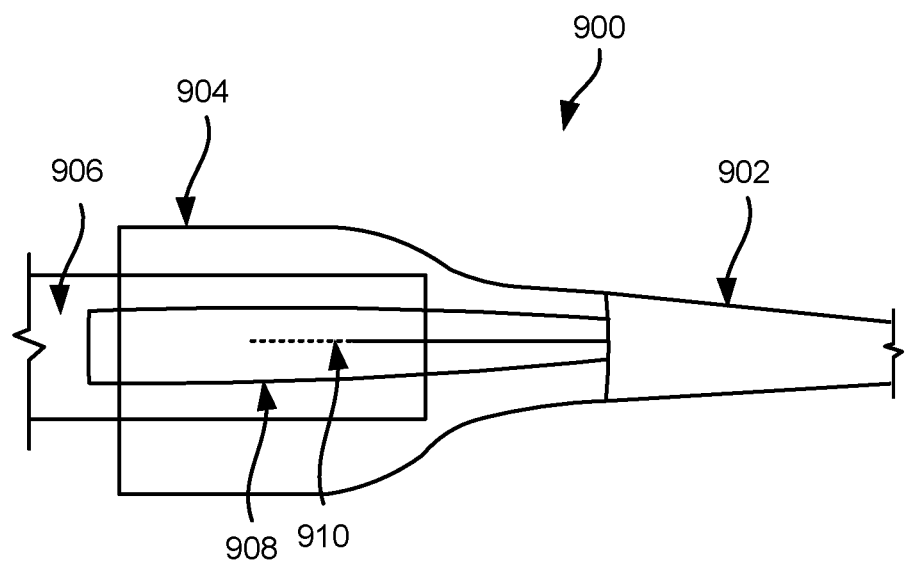
FIG. 9 is a top view of a portion of a medical device assembly, according to an embodiment of the invention.
Figure 10:
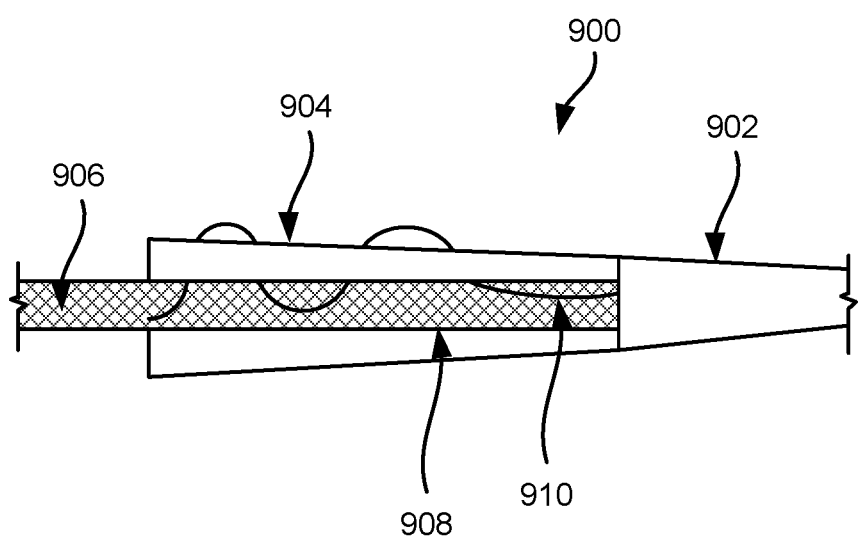
FIG. 10 is a side view of the portion of the medical device assembly of FIG. 9.

FIG. 9 is a top view of a portion of a medical device assembly 900, according to an embodiment of the invention. The medical device assembly 900 includes a dilator 902, a sleeve 904 and an arm portion 906. A first suture 908 and a second suture 910 are bonded at one end with the dilator 902 and the sleeve 904. The other end of the first suture 908 and the second suture 910 travels back toward the arm portion 906. At the arm portion 906, the first suture 908 and/or the second suture 910 are woven through the sleeve 904 and the arm portion 906 as shown in the FIG. 10 (which is a side view of the medical device assembly of FIG. 9). The weaving provides resistance to the arm portion 906 upon release as the physicians pulls the dilator 902 and sleeve 904. The second suture 910 terminates within the area of the arm portion 906 (not connected or fixed). In an embodiment, the first suture 908 forms a loop, and at least a portion of the first suture 908 is woven through a portion of the arm portion 906, wherein at least a portion of the second suture 910 is woven along a longitudinal axis of the arm portion 906.

Once the implant is placed, the physician cuts a single strand of the first suture 908. The sleeve 904 (and the dilator 902 that is coupled to the sleeve 904) can then be pulled off of the arm portion 906 by pulling on the sleeve 904 and the uncut strand of the first suture 908. The cut portion of the first suture 908 will be free to pull through the arm portion 906. Since, the second suture 910 is woven through the arm portion 906 and the sleeve 904; the second suture 910 is also free to be pulled out. Thus, the first suture 908 and the second suture 910 remain secured to the sleeve 904 and will simply unravel or unthread themselves from the arm portion 906.

Figure 11:
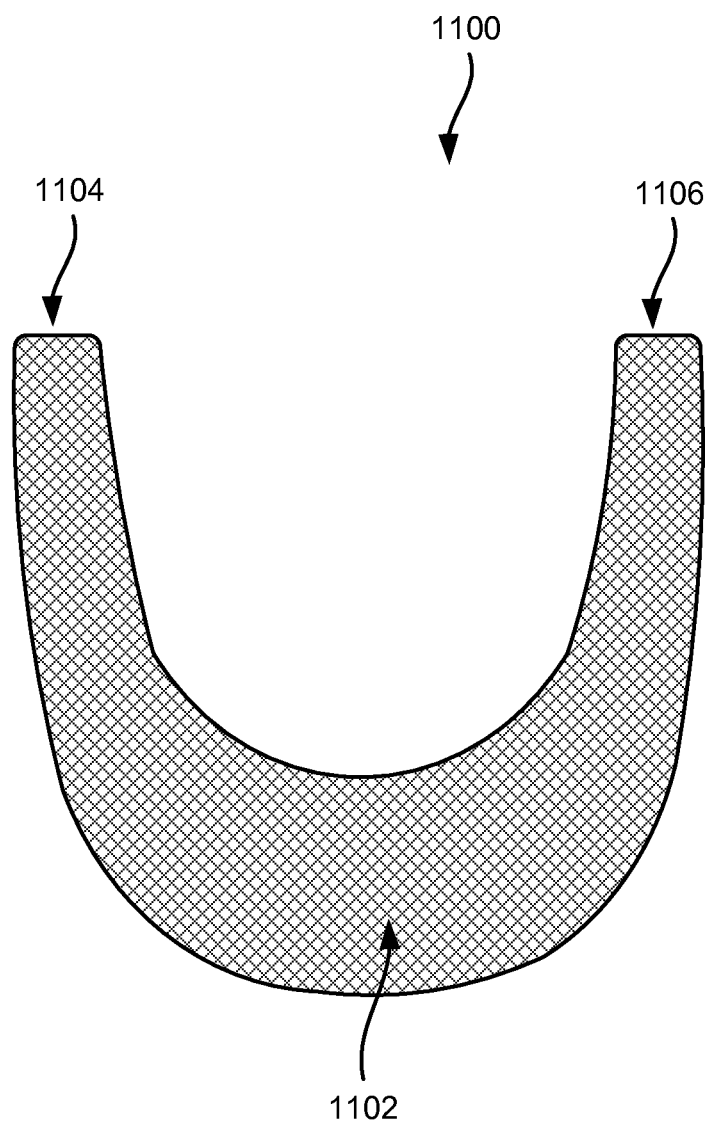
FIG. 11 is a top view of an implant according to an embodiment of the invention.

FIG. 11 is a top view of an implant 1100 according to an embodiment. The implant 1100 includes a support portion 1102, a first arm portion 1104 and a second arm portion 1106. The support portion 1102 of the implant 1100 is functionally similar to the support portion 222 of the implant 220 described above. The first arm portion 1104 and the second arm portion 1106 are functionally similar to the arm portion 234 of the implant 220 described above. The first arm portion 1104 and the second arm portion 1106 are configured to support the support portion 1102 when the first arm portion 1104 and the second arm portion 1106 are disposed within a tissue of a patient.

Although two arm portions are illustrated, the implant 1100 may be of any shape and may be used at various locations in the body. In addition, the implant 1100 may include any number of arm portions. For example, in some embodiments, the implant 1100 includes a single arm portion. In other embodiments, the implant 1100 includes more than two arm portions. In some embodiments, the implant 1100 includes exactly two arm portions, which may be used to support a uterus or a vaginal vault.

The first arm portion 1104 is inserted into the first portion of the SSL using a first sleeve and a first dilator. A first suture has a first portion coupled to the first arm portion 1104, and a second portion coupled to the first dilator. A second suture having a first portion coupled to the first arm portion 1104, and a second portion coupled to the first dilator. A delivery device, such as those described above, can be used to aid in inserting the first arm portion 1104 into the SSL. Once the first arm portion 1104 (still covered by a sleeve) is disposed within the SSL, the second arm portion 1106 can be inserted into a second portion of the SSL using a second sleeve and a second dilator. A third suture has a first portion coupled to the second arm portion 1106, and a second portion coupled to the second dilator. A fourth suture has a first portion coupled to the second arm portion 1106, and a second portion coupled to the second dilator.

Once the first and second sleeves are removed from the first arm portion 1104 and the second arm portion 1106, respectively, the first arm portion 1104 and the second arm portion 1106 engage with the surrounding tissue and support the support portion 1102 in the pelvic region of the patient. Any excess portion of the arm portions can be cut and/or removed.

Figure 12:
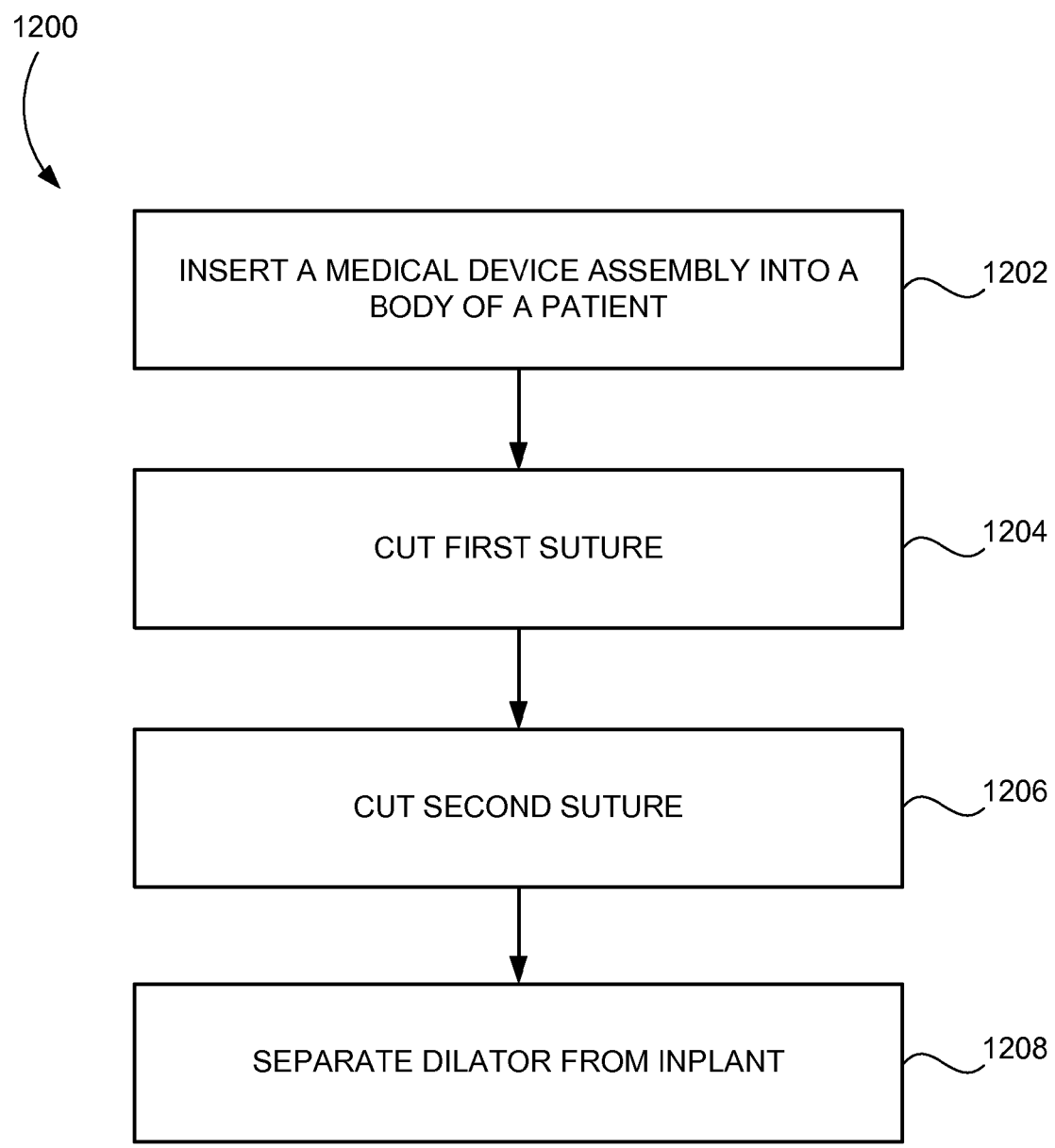
FIG. 12 is flow chart of a method of placing an implant within a body of a patient according to an embodiment of the invention.

FIG. 12 is flow chart of a method 1200 for placing a medical device assembly within a body of a patient, according to an embodiment of the invention. As described above, the medical device assembly includes an implant having a support portion and an arm portion, a dilator, a first suture having a first portion coupled to the arm portion of the implant and a second portion coupled to the dilator, and a second suture having a first portion coupled to the arm portion of the implant and a second portion coupled to the dilator. In an embodiment, the first suture forms a loop, and at least a portion of the first suture is woven through a portion of the arm portion of the implant. Further, at least a portion of the second suture is woven through a portion of the arm portion of the implant.

At step 1202, a physician inserts the medical device assembly into the body of the patient, such that a first portion of the medical device assembly is disposed within the body of the patient, and a second portion of the medical device assembly is disposed outside of the body of the patient. In an embodiment, the arm portion 234 (see FIG. 3A) is placed through a selected tissue site and adjusted as described above.

Therefore, at step 1204, the physician cuts the first suture 242 within the sleeve 226. For example, one strand of the loop formed by the first suture 242 is cut. Similarly, at step 1206, the physician cuts the second suture 254 within the sleeve 226. In some embodiments, the sutures 242 and 254 may be cut by the physician at the same time or simultaneously. Again, one strand of the loop formed by the second suture 254 is cut. Since the arm portion 234 is coupled to the sleeve 226 via the first and the second sutures 242 and 254, cutting the sutures 242 and 254 allows free movement of the sleeve 226 relative to the corresponding arm portion 234.

Finally, at step 1208, the physician separates the sleeve assembly (including the sleeve 226 the dilator 228) and the arm portion 234 by pulling on the sleeve assembly and the uncut strand of the first suture 242 and/or the second suture 254. The cut first suture 242 and the cut second suture 254 will also be free to pull through the arm portion 234. Thus, the first suture 242 and the second suture 254 remain secured to the sleeve assembly and will simply unravel or unthread itself from the arm portion 234. When the sleeves 226 are removed, the arm portions 234, 236 and 238 engage the surrounding tissue into which the arm portions 234, 236 and 238 have been placed. The tangs or dimples on the arm portions 234, 236 and 238 can also engage surrounding tissue.

In some embodiments (wherein the implant shaped as in FIG. 2), the posterior support portion 246 can be positioned around a vaginal cuff before or after removing the sleeves 226 from the arm portions 234, 236, 238. A posterior vaginal incision may be made to provide access for positioning the posterior support portion 246. For example, a physician can access the posterior support portion 246 via a posterior incision and using a hand can tuck or wrap the posterior support portion 246 around a vaginal cuff in a posterior region of the pelvis between the vagina and a rectum of a patient. The posterior support portion 246 can also optionally be secured to tissue or ligament within the pelvic region. For example, the posterior support portion can be sutured or stitched to a rectovaginal septum or a perineal body.

In further embodiments, the order in which the arm portions (234, 236, 238) are placed can vary. In one example of the order of delivering the arm portions, the posterior arm portions 238 are first delivered on each side of the pelvic region, and placed within, for example, SSL. Then, the mid arm portions 236 are delivered and placed within an arcus tendineus. The anterior arm portions 234 are then delivered and placed within either the arcus tendineus or an obturator (e.g., obturator muscle or membrane). The location of the dilator 228 during the delivery process can be used to distinctively identify which the dilator 228 has been passed through which tissue (e.g., arcus tendineus, obturator). For example, a location of a dilator exiting a vaginal anterior incision relative to the vagina (e.g., along a side, near the top, or near the bottom) can help indicate which tissue securement site corresponds to which dilator. For example, a dilator extending from a side of the vagina can indicate that the dilator was placed through the patient's arcus tendineus.

The order of tensioning of the arm portions can also vary. In yet further embodiments, the anterior arm portions 234 can be tensioned first, then the mid arm portions 236, and lastly the posterior arm portions 238. The anterior arm portions 234 can be used to position the anterior support portion 244 longitudinally and laterally. The mid arm portions 236 can be used, for example, to adjust and position the posterior support portion 148. The posterior arm portions 238 can provide a "deeper" anchor point and a proper angle for vaginal support.

In some embodiments, a medical device assembly includes an implant having a support portion and an arm portion; a dilator; a first suture having a first portion coupled to the arm portion of the implant and a second portion coupled to the dilator; and a second suture having a first portion coupled to the arm portion of the implant and a second portion coupled to the dilator.

In some embodiments, the assembly includes a sleeve. The sleeve is coupled to the dilator. The sleeve defines a cavity. At least a portion of the arm portion of the implant is disposed within the cavity defined by the sleeve.

In some embodiments, the assembly includes a sleeve. The sleeve is coupled to the dilator. The sleeve defines a cavity. At least a portion of the arm portion of the implant is disposed within the cavity defined by the sleeve. At least a portion of the first suture is disposed within the cavity defined by the sleeve. At least a portion of the second suture is disposed within the cavity of the sleeve.

In some embodiments, the assembly includes an association member coupled to the dilator. The association member is configured to associate the assembly to a delivery device.

In some embodiments, the first portion of the first suture is coupled to the arm portion of the implant at a first location, and the first portion of the second suture is coupled to the arm portion of the implant at a second location different than the first location.

In some embodiments, the first portion of the first suture is coupled to the arm portion of the implant at a first location, and the first portion of the second suture is coupled to the arm portion of the implant at a second location different than the first location, the first location being disposed between the second location and the support portion of the implant.

In some embodiments, the first suture is woven through a portion of the arm portion of the implant and forms a loop, and the second suture is woven through a portion of the arm portion of the implant and forms a loop.

In some embodiments, the first suture forms a loop and the second suture has a first end coupled to the dilator and second end disposed away from the dilator.

In some embodiments, the first suture forms a loop and the second suture has a first end coupled to the dilator and a second end coupled to the arm portion of the implant.

In some embodiments, the first suture forms a loop and at least a portion of the first suture is woven through a portion of the arm portion of the implant, and at least a portion of the second suture is woven along a longitudinal axis of the arm portion of the implant.

In some embodiments, the arm portion of the implant is a first arm portion, the dilator is a first dilator, the implant including a second arm portion, the assembly further including: a second dilator; a third suture having a first portion coupled to the arm portion of the implant and a second portion coupled to the dilator; and a fourth suture having a first portion coupled to the arm portion of the implant and a second portion coupled to the dilator.

In some embodiments, a medical device assembly includes an implant having a support portion and an arm portion; a dilator; a sleeve coupled to the dilator; a first suture having a first portion coupled to the arm portion of the implant and a second portion coupled to the dilator; and a second suture having a first portion coupled to the arm portion of the implant and a second portion coupled to the dilator, the second suture being woven through a portion of the sleeve and a portion of the arm portion of the implant.

In some embodiments, the sleeve defines a cavity, and at least a portion of the arm portion of the implant being disposed within the cavity defined by the sleeve.

In some embodiments, the sleeve defines a cavity, at least a portion of the arm portion of the implant being disposed within the cavity defined by the sleeve, and at least a portion of the first suture being disposed within the cavity defined by the sleeve.

In some embodiments, a first end portion of the first suture is coupled to the dilator and a second end portion of the first suture is coupled to the dilator such that the first suture forms a loop. In some embodiments, the first suture forms a loop.

In some embodiments, the first suture forms a loop and a least a portion of the first suture is woven through a portion of the arm portion of the implant.

In some embodiments, a method of placing an implant within a body of a patient includes inserting an assembly into a body of a patient such that a first portion of the assembly is disposed within the body of the patient and a second portion of the assembly is disposed outside of the body of the patient, the assembly including an implant having a support portion and an arm portion, a dilator, a first suture having a first portion coupled to the arm portion of the implant and a second portion coupled to the dilator, and a second suture having a first portion coupled to the arm portion of the implant and a second portion coupled to the dilator; cutting the first suture; cutting the second suture; and separating the dilator from the implant such that at least a portion of the implant remains within the body of the patient.

In some embodiments, the first suture forms a loop and at least a portion of the first suture is woven through a portion of the arm portion of the implant.

In some embodiments, the first suture forms a loop and at least a portion of the first suture is woven through a portion of the arm portion of the implant, at least a portion of the second suture is woven through a portion of the arm portion of the implant.

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

What is claimed is:

1. A medical device assembly, comprising:
   an implant having a support portion and an arm portion;
   a dilator;
   a sleeve coupled to the dilator;
   a first suture having a first portion coupled to the arm portion of the implant and a second portion coupled to the dilator, the first suture forming an outer loop along the arm portion and within the sleeve, the outer loop having a first strand and a second strand; and
   a second suture having a first portion directly connected to the arm portion of the implant and a second portion directly connected to the dilator, the second suture forming an inner loop along the arm portion and within the sleeve, the inner loop being disposed between the first strand of the outer loop and the second strand of the outer loop.

2. The assembly of claim 1, wherein the sleeve defines a cavity, at least a portion of the arm portion of the implant being disposed within the cavity defined by the sleeve.

3. The assembly of claim 1,
   wherein the sleeve defines a cavity, at least a portion of the arm portion of the implant being disposed within the cavity defined by the sleeve, at least a portion of the first suture being disposed within the cavity defined by the sleeve, at least a portion of the second suture being disposed within the cavity of the sleeve.

4. The assembly of claim 1, further comprising:
   an association member coupled to the dilator, the association member being configured to associate the assembly to a delivery device.

5. The assembly of claim 1, wherein the first portion of the first suture is coupled to the arm portion of the implant at a first location on the arm portion, the first portion of the second suture is coupled to the arm portion of the implant at a second location on the arm portion different than the first location.

6. The assembly of claim 1, wherein the first portion of the first suture is coupled to the arm portion of the implant at a first location on the arm portion, the first portion of the second suture is coupled to the arm portion of the implant at a second location on the arm portion different than the first location, the first location being disposed between the second location and the support portion of the implant.

7. The assembly of claim 1, wherein a portion of the outer loop of the first suture is woven through a portion of the arm portion of the implant at a first location of the implant, and a portion of the inner loop of the second suture is woven through a portion of the arm portion of the implant at a second location of the implant.

8. The assembly of claim 1, wherein ends of the second suture are coupled to an interior wall of the dilator, and ends of the first suture are coupled to the interior wall of the dilator.

9. The assembly of claim 1, wherein at least a portion of the first suture is woven through a portion of the arm portion of the implant, at least a portion of the second suture is woven along a longitudinal axis of the arm portion of the implant.

10. The assembly of claim 1, wherein the arm portion of the implant is a first arm portion, the dilator is a first dilator, and the implant includes a second arm portion, the assembly further comprising:
a second dilator;
a third suture having a first portion coupled to the arm portion of the implant and a second portion coupled to the dilator; and
a fourth suture having a first portion coupled to the arm portion of the implant and a second portion coupled to the dilator.

11. A medical device assembly, comprising:
an implant having a support portion and an arm portion;
a dilator;
a sleeve coupled to the dilator;
a first suture having a first portion coupled to the arm portion of the implant and a second portion coupled to the dilator, the first suture forming an outer loop along the arm portion and within the sleeve, the outer loop having a first strand and a second strand; and
a second suture having a first portion directly connected to the arm portion of the implant and a second portion directly connected to the dilator, the second suture being woven through a portion of the sleeve and a portion of the arm portion of the implant, the second suture forming an inner loop along the arm portion and within the sleeve, the inner loop being disposed between the first strand of the outer loop and the second strand of the outer loop.

12. The assembly of claim 11, wherein the sleeve defines a cavity, at least a portion of the arm portion of the implant being disposed within the cavity defined by the sleeve.

13. The assembly of claim 11, wherein the sleeve defines a cavity, at least a portion of the arm portion of the implant being disposed within the cavity defined by the sleeve, at least a portion of the first suture being disposed within the cavity defined by the sleeve.

14. The assembly of claim 11, wherein a first end portion of the first suture is coupled to an interior wall of the dilator and a second end portion of the first suture is coupled to the interior wall of the dilator, the first suture looping back at a first location on the arm portion to form the outer loop, wherein a first end portion of the second suture is coupled to the interior wall of the dilator and a second end portion of the second suture is coupled to the interior wall of the dilator, the second suture looping back at a second location on the arm portion to form the inner loop.

15. The assembly of claim 11, wherein at least a portion of the first suture is woven through a portion of the arm portion of the implant.

* * * * *